United States Patent
Sharma et al.

(10) Patent No.: US 7,711,497 B2
(45) Date of Patent: May 4, 2010

(54) METHOD OF IDENTIFYING CALCIUM-BINDING SITES IN GAMMA-CRYSTALLIN USEFUL FOR MANAGEMENT OF CATARACT

(75) Inventors: Yogendra Sharma, Hyderabad (IN); Bheemreddy Rajini Devi, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 433 days.

(21) Appl. No.: 10/350,558

(22) Filed: Jan. 24, 2003

(65) Prior Publication Data

US 2004/0053338 A1 Mar. 18, 2004

Related U.S. Application Data

(60) Provisional application No. 60/351,682, filed on Jan. 25, 2002.

(51) Int. Cl.
*G06F 19/00* (2006.01)

(52) U.S. Cl. .................................................... 702/27

(58) Field of Classification Search .................. 702/27, 702/19

See application file for complete search history.

(56) References Cited

OTHER PUBLICATIONS

Drenth, Jan. Principles of Protein Crystallography. Springer-Verlag: New York (1994), pp. 1-18.*
Service, Robert. "Tapping DNA for Structures Produces a Trickle", Science, vol. 298, Nov. 2002, pp. 948-950.*
Bheemreddy Rajini, et al., Calcium Binding Properties of γ-Crystallin, Calcium Ion Binds At the Greek Key by-Crystallin Fold, The Journal of Biological Chemistry, vol. 276, No. 42, Issue of Oct. 19, 2001, pp. 38464-38471.

* cited by examiner

*Primary Examiner*—Jerry Lin
(74) *Attorney, Agent, or Firm*—Arent Fox LLP

(57) ABSTRACT

The present invention relates to a method of identifying calcium binding sites in gamma-crystallin useful in calcium-based homeostasis for the management of Cataract, said method comprising steps of isolating gamma-crystallin from eye lens, studying binding of calcium to the isolated protein by both direct and indirect methods, identifying Greek key Motif as calcium-binding sites of the protein gamma crystallin with the said protein binding 4-mol eq of calcium having dissociation constant of 90 micromole.

12 Claims, 10 Drawing Sheets

Figure 1A:
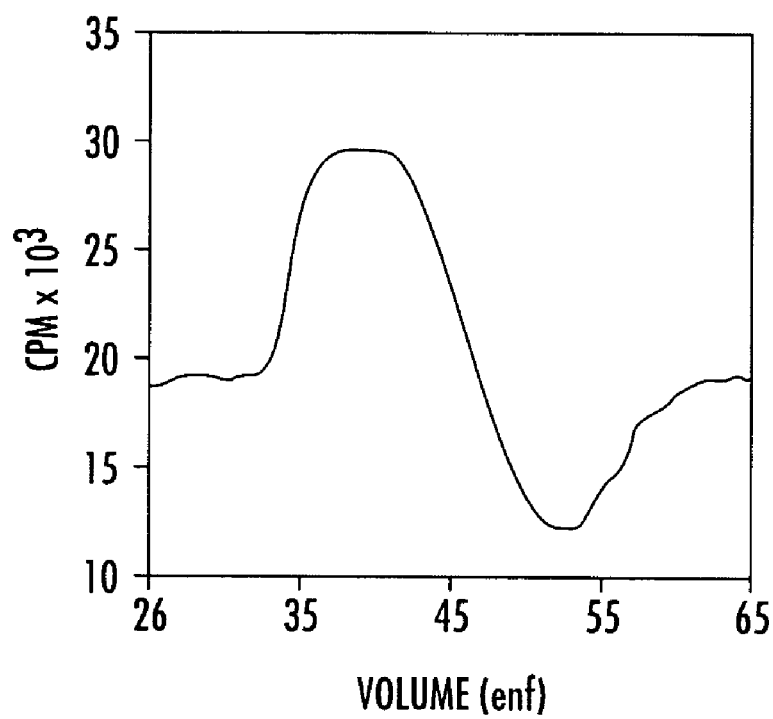

| | | | |
|---|---|---|---|
| PS1 | 1 | ANITVFYNEDFQGKQVDLPPGNYTRAQLAAIGIENNTISSVKVPP | 45 | (SEQ. ID NO. 5) |
| G2 | 40 | GCWMLVERPNYQGHQYFLRRGDYPDYQ--QWMGFNDSIRSCRLI | 81 | (SEQ. ID NO. 6) |
| PS3 | 91 | PRARFFYKEQFDGKEVDLPPGQYTQAELERYGIDNNTISSVKPQG | 135 | (SEQ. ID NO. 7) |
| G4 | 130 | GSWVLVEMPSYRGRQYLLRPGEYRRYL--DWGAMNAKVGSLRRVM | 172 | (SEQ. ID NO. 8) |
| PS2 | 47 | VKAILVQNDGFAGDQIEVVA-MAEEL------GPLNNNVSSIRVIS | 85 | (SEQ. ID NO. 9) |
| G1 | 1 | GKITFVEDRGFQGHCYECSS-DCPNL-----QPYFSRCNSIRVDS | 39 | (SEQ. ID NO.10) |
| PS4 | 136 | LAVVLFKNDNFSGDTLPVNS-DAPLT-----GAMNNNTSSIRIS | 173 | (SEQ. ID NO.11) |
| G3 | 88 | FRMRIVERDOFRGQMSEITD-DCPSL-----QDRFHLTEVHSLNVLE | 129 | (SEQ. ID NO.12) |
| ep37a1 | 3 | NTITVVEHSDFRGLYKTFTS-DVPNL-----VYENFNDCISSVKIAG | 43 | (SEQ. ID NO.13) |
| ep37a2 | 1 | NTITVVEHPNFQGLSRTFTT-DVPRL-----SEHSFEDCISSAKVVG | 41 | (SEQ. ID NO.14) |
| ep37L2 | 3 | NTITVVEHSNFQGLHKTFTA-DVPNL-----VNESFNDCISSVKIVG | 43 | (SEQ. ID NO.15) |
| BB2 | 16 | PKIIIFEQENFQGHSHELNG-PCPNLKETG----VEKAGSVLVQA | 55 | (SEQ. ID NO.16) |
| WmKT | 47 | GCATIWBGSGCVGRSTTMCC--PANTCCN---INTGFYIRSYRRVE | 87 | (SEQ. ID NO.17) |
| AIM1 | 1275 | GVWVAVENPDFTSEQYIL-DKGFYTSFE-DWGGKNYKISSVQP | 1315 | (SEQ. ID NO.18) |

FIG. 4

METHOD OF IDENTIFYING CALCIUM-BINDING SITES IN GAMMA-CRYSTALLIN USEFUL FOR MANAGEMENT OF CATARACT

CROSS REFERENCE TO RELATED APPLICATION

This application claims the benefit under 35 U.S.C. 119(e) of U.S. Provisional Patent Application No. 60/351,682, filed Jan. 25, 2002, the entirety of which is hereby incorporated by reference into this application.

FIELD OF THE INVENTION

The present invention relates to a method of identifying calcium binding sites in gamma-crystallin useful in calcium-based homeostasis for the management of Cataract, said method comprising steps of isolating gamma-crystallin from eye lens, studying binding of calcium to the isolated protein by both direct and indirect methods, identifying Greek key Motif as calcium-binding sites of the protein gamma crystallin with the protein binding 4-mol eq of calcium having dissociation constant of 90 micromole.

BACKGROUND AND PRIOR ART REFERENCES

Calcium homeostasis plays an important role in lens transparency, opacification, and cataractogenesis. Cataracts can occur both under hypocalcemic and hypercalcemic conditions, so the actual amount of available calcium in the lens is an important parameter for the health of the lens (1, 2). The normal mammalian lens has around 0.2-mM total calcium, of which the amount of free $Ca^{2+}$ is only of the order of a few micromolars. Thus there must exist calcium regulation systems in the lens, and it is of interest to identify what they are and how they change in health and in disease. Vrensen et al. (3) have done an ultrastructural analysis of calcium distribution in the rat lens and have found calcium precipitates in the intermediate cortex fiber membranes, cytoplasm, and the nuclear envelope and very low levels of calcium in gap junctions, epithelial cells, and superficial fibers (3-5). The question of what the calcium-binding and -storing agents are in the lens is open; phospholipids and crystallins have been thought of as candidates. The major components of the lens are cytosolic proteins, crystallins, which account for about 40% of the wet weight of the lens. It is worth investigating whether any of the crystallins could act as; calcium sponge or storage depot in the tissue, particularly sine the ultrastructural analysis shows calcium distribution in the cytoplasm. We have earlier shown that the beta and avian core protein delta-crystallins show significant calcium-binding ability; (6, 7). Thus, the possibility of crystallins acting as lenticular calcium-sequestering and -storing systems exists.

However the calcium binding properties of gamma-crystallin have not yet been reported.

Gamma-Crystallin is a well-studied protein and was the first crystallin whose structure was solved (8). The Greek key crystallin fold was first described in this protein (8). It was later found in another lens protein, beta-crystallin, and in several other non-lens proteins, which were together classified as the beta-gamma-crystallin superfamily (9,10). The crystallin fold, also called the beta-gamma motif is a super-secondary structure formed from the symmetrical association of the two Greek key motifs that are organized into a two four-stranded anti-parallel beta-sheets (8, 9). The crystallin fold is a protein domain in which aromatic residues Tyr/Phe/Trp at position 1 and Gly at position 8 constitute the conserved sequence (Y/F/W) XXXXXXG, followed by a Ser at positions 28-34 from the first Y/F/W residue, and this sequence is repeated within 40 residues. Gly-8 is irreplaceable and is needed for forming a dihedral angle, which is not possible with another amino acid. These residues are required for the stabilization of the folded hairpin of the beta-gamma motif (11). Between Gly-8 and Ser-34 lie two charge clusters of alternate signs (12).

More members have been added to the diverse beta-gamma-crystallin superfamily. Protein S, a development-specific protein from *Myxococcus xanthus* (13-15), spherulin 3a from *Physarun polycephalum* (16, 17), AIM1 (absent in melanoma) which is associated with the tumorigenicity in human malignant melanoma (18), epidermis differentiation-specific protein family; (EDSP or EP37) from the amphibian *Cynops pyrrhogaster* (19-21), a yeast killer toxin (WmKT) from *Williopsis mrakii* (22) *Streptomyces* metalloproteinase inhibitor (SMPI) (23), and the calmodulin-binding membrane protein family (PCM) from *Paramecium tetraurelia* (24) are the non-lens members of the beta-gamma crystallin superfamily. Beta-gamma-Crystallins are thought to have originated from a single domain ancestor by gene duplication and gene fusion (25). The beta-gamma motif is seen in single domain (spherulin 3a and WmKT), two domain (beta- and gamma-crystallins, protein S EP37, SMPI) as well as multi-domain proteins (AIM1). Evolutionarily, these proteins are among the most long-lived globular proteins known, generally expressed under stressed, adverse conditions or in differentiating tissues.

Table 1
Amino acid sequence of the Greek key crystallin fold peptide (corresponding to the third Greek key of bovine gamma-crystallin) and its mutants were synthesized and studied for calcium binding. Peptide s3a is the peptide corresponding to the first Greek key motif of spherulin 3a. Bold letters indicate the mutation of the residues.

TABLE I

| Peptides | Amino acid sequence | Seq. ID No. |
|---|---|---|
| g3  | $^{90}$RMRIYERDDFRGQMSEITDDCPSLQDRFHLTEVHSLNVLEGS$^{131}$ | 1 |
| g3a | $^{90}$RMRIYKRDDFRGQMSEITDDCPSLQDRFHLTKVHSLNVLEGS$^{131}$ | 2 |
| g3b | $^{90}$RMRIYERDDFRGQMSEITKKCPSLQDRFHLTEVHSLNVLEGS$^{131}$ | 3 |
| g3a | $^{14}$GEVFLYKHVNFQGDSWKVTGNVYDFRSVSGLNDVVSSVKVGPN$^{56}$ | 4 |

It is believed that the crystallin domain evolved in proteins of extraordinary stability. Members of this superfamily have, therefore, been studied for their stability and architecture. An interesting feature of some of these proteins is their calcium-binding ability, e.g. beta-crystallin (6, 7, 26), protein S (14, 27), and spherulin 3a (17). Putative calcium-binding sites have been shown in the EP37 protein (20). However, these proteins do not have any of the well-characterized motifs for calcium binding, such as the EF-hand, lipocortin-, or the annexin-like domains. They thus seem to contain an "orphan" motif, which needs to be identified.

Surprisingly, the calcium-binding ability of gamma-crystallin is not yet known, although it is the representative model of the superfamily, whose three-dimensional structure is very well known. Studying the calcium binding to gamma-crystallin not only points to the inherent characteristic of the superfamily but would also help in identifying the orphan motif in the members of beta-gamma-crystallin superfamily. In this work, we report that gamma-crystallin does bind calcium. We also show that the Greek key crystallin fold forms the calcium-binding site. Since members of this superfamily share a homologous crystallin fold, we suggest that other members also bind calcium and thus represent a novel class of calcium-binding proteins.

OBJECTS OF THE PRESENT INVENTION

The main object of the present invention is to develop a method of identifying calcium binding sites in gamma-crystallin useful in calcium-based homeostasis for the management of Cataract.

Another main object of the present invention is to study binding of calcium to the isolated protein by both direct and indirect methods.

Yet another object of the present invention is to identifying Greek key Motif as calcium-binding sites of the protein gamma crystallin with the protein binding 4-mol eq of calcium with a dissociation constant of 90 micromole.

Still another object of the present invention is to study the effect of binding on conformation of secondary and tertiary structure of the protein.

Still another object of the present invention is to determine the exact calcium-binding site on the motif.

Still another object of the invention is to determine the number of sites of calcium binding in gamma crystallin.

Still another object of the present invention is to compare calcium-binding affinity of gamma-crystallin with beta-crystallin.

Still another object of the present invention is to determine the effect of calcium-binding on stability of gamma-crystallin.

SUMMARY OF THE PRESENT INVENTION

The present invention relates to a method of identifying calcium binding sites in gamma-crystallin useful in calcium-based homeostasis for the management of Cataract, said method comprising steps of isolating gamma-crystallin from eye lens, studying binding of calcium to the isolated protein by both direct and indirect methods, identifying Greek key Motif as calcium-binding sites of the protein gamma crystallin with the protein binding 4-mol eq of calcium having dissociation constant of 90 micromole.

DETAILED DESCRIPTION OF THE PRESENT INVENTION

Accordingly, the present invention relates to a method of identifying calcium binding sites in gamma-crystallin useful in calcium-based homeostasis for the management of Cataract, said method comprising steps of isolating gamma-crystallin from eye lens, studying binding of calcium to the isolated protein by both direct and indirect methods, identifying Greek key Motif as calcium-binding sites of the protein gamma crystallin with the protein binding 4-mol eq of calcium having dissociation constant of 90 micromole.

In an embodiment of the present invention, wherein a method of identifying calcium binding sites in gamma-crystallin useful in calcium-based homeostasis for the management of Cataract, said method comprising steps of isolating gamma-crystallin from eye lens, studying binding of calcium to the isolated protein by both direct and indirect methods, identifying Greek key Motif as calcium-binding sites of the protein gamma crystallin with the protein binding 4-mol eq of calcium with a dissociation constant of 90 micromole.

In another embodiment of the present invention, wherein the binding does not affect conformation of secondary and tertiary structure of the protein.

In yet another embodiment of the present invention, wherein the amino acid adjacent to the conserved aromatic corner in the "a" strand and three amino acids of the "d" strand participate in calcium binding.

In still another embodiment of the present invention, wherein beta-gamma crystallin superfamily represents a novel class of calcium binding proteins.

In still another embodiment of the present invention, wherein the said protein shows four sites of calcium binding.

In still another embodiment of the present invention, wherein the direct and indirect methods are Hummel-Dreyer method and terbium fluorescence method respectively.

In still another embodiment of the present invention, wherein the Greek key crystallin fold is the site for ion-exchange.

In still another embodiment of the present invention, wherein the binding affinity of calcium to gamma-crystallin is more than that of beta-crystallin.

In still another embodiment of the present invention, wherein the first calcium ligates at the residue next to the conserved aromatic amino acid of the sequence Y/F/WXXXXXXG, which is located at the end of the first beta-strand ("a" strand); the amino-acid at this position is generally Asp, Asn, Glu, Gin, Ser, Tyr, and rarely Lys.

In still another embodiment of the present invention, wherein the other three residues needed for calcium ligation lie just before the beginning of the fourth bet-strand (before the conserved Ser) and are usually Asp, Asn, Thr, Val, or Ala.

In still another embodiment of the present invention, wherein all the members of the beta-gamma superfamily bind to calcium.

In still another embodiment of the present invention, wherein the crystallin fold is a novel calcium-binding motif.

In still another embodiment of the present invention, wherein binding of calcium restricts unfolding of the gamma-crystallin.

In still another embodiment of the present invention, wherein stability of gamma-crystallin increases in the presence of calcium ions.

In still another embodiment of the present invention, wherein calcium binding ensures steady cytosolic level of calcium.

In still another embodiment of the present invention, wherein The beta and gamma crystallins are closely related lens proteins that are members of the beta-gamma-crystallin superfamily, which also include many non-lens members. Although beta-crystallin is known to be a calcium-binding protein, this property has not been reported in gamma crystallin. We have studied the calcium binding properties of gamma-crystallin, and we show that it binds 4 mol eq of calcium with a dissociation constant of 90 micromole. It also binds the calcium-mimic spectral probes, terbium and Stains-all. Calcium binding does not significantly influence protein secondary and tertiary structures.

In still another embodiment of the present invention, wherein We present evidence that the Greek key crystallin fold is the site for calcium ion binding in gamma-crystallin. Peptides corresponding to Greek key motif of gamma-crystallin (42 residues) and their mutants were synthesized and studied for calcium binding. These peptides adopt beta-sheet conformation and form aggregates producing beta-sandwich. Our results with peptides show that, in Greek key motif, the amino acid adjacent to the conserved aromatic corner in the "a" strand and three amino acids of the "d" strand participate in calcium binding. We suggest that the beat-gamma superfamily represent a novel class of calcium-binding proteins with the Greek key beta-gamma crystallin fold as potential calcium-binding sites. These results are of significance in understanding the mechanism of calcium homeostasis in the lens.

Experimental Procedures

In still another embodiment of the present invention, wherein All chemicals used were of the analytical grade. Terbium chloride was obtained from Aldrich and Stains-all from Sigma. Radioactive calcium chloride ($^{45}CaCl2$, specific activity 11.7 mCi/mg) was purchased from Perkin-Elmer Life Sciences.

Preparation of Crystallins-Bovine eyes were collected from animals (age 3-5 years) from a local slaughterhouse and brought to the laboratory on ice. Lenses were excised and homogenized in the gel filtration buffer. gamma-Crystallin from bovine lenses was purified on a Bio-Gel A-1.5 m column (2.5×90 cm) in SO mM Tris buffer, pH 7.5, 100 mM NaCl, 1 ran EDTA, 0.02% sodium azide at 4° C. Solutions of crystallins were rendered calcium-free by dialyzing first against EDTA at pH 2 and then against calcium-free water. Protein solutions were concentrated using an Amicon ultrafiltration unit with YM-10 membrane. Finally, protein and buffer solutions were passed through Chelex-100 columns before use, so as to remove any calcium that might be present as a contaminant and stored in plastic ware. Protein concentrations were calculated from their absorption coefficients.

Design and Synthesis of Four-stranded Greek Key Beta-Sheet Peptides-We have selected a stretch of 42 amino acids corresponding to the third motif of the bovine gamma II-crystallin (residues 90-131) to have a complete geometry of the Greek key crystallin fold. We have synthesized the wild type and its variants by modifying the potential residues by replacing them with Lys to see if these amino acids affect the binding affinity. We have alto synthesized a 42-residue peptide corresponding to 14-56 amino acid residues of spherulin 3a to use as a control. The sequences of the synthetic peptides studied in the present work are reported in Table 1. These peptides were synthesized according to the solid-phase procedure of Merrifield (28) with minor modifications (29). The peptides were purified on HPLC and collected as more than 99% pure. The purity and analysis of synthesized peptides were done on mass spectroscopy as well as by sequence analysis. The aggregational properties of these peptides were evaluated on gel filtration HPLC using the column, Protein-Pak 125 (Waters Associates, Millipore), in 50 mM Tris. pH 6.8, containing 50 mw NaCl.

$^{45}$Ca Binding Studies by Hummel-Dreyer Method—The binding of $^{45}$Ca to gamma-crystallin was studied by the gel filtration method of Hummel and Dreyer (30). Plastic containers, tubes, and bottles were used to avoid $Ca^{2+}$ contamination from laboratory glassware. Protein solutions were equilibrated with $^{45}$Ca for 1 h at room temperature and applied to Sephadex G-25 columns (25×2 cm) that had been equilibrated earlier with 50 mM Tris buffer, pH 7.1, 60 mM NaCl containing varying amounts of (25-100 microM) calcium chloride solution (including $^{45}$Ca). Fractions of 1 ml were collected, and total radioactivity in each fraction was counted for $^{45}$Ca in a Hewlett-Packard liquid scintillation counter. Bound $Ca^{2+}$ concentration was determined using the area of the radioactive peak corresponding to protein-bound $^{45}$Ca and the accompanying trough. Klotz plots (inverse plot, I/r versus I/A) of the data collected at different free $Ca^{2+}$ concentrations were used to estimate the binding constants (31, 32).

Calcium Binding Studies by $^{45}$Ca Overlay Method-Calcium binding to peptides was done by $^{45}$Ca overlay method of Maruyama et al, 133). 20-50 fig of peptides were spotted onto a polyvinylidene difluoride membrane by dot-blot apparatus. The membrane was equilibrated in a solution containing 10-mM imidazole HCl. pH 6.8, 60 mM KCl, 5 mM $MgCl_2$ and then incubated for 15 min at 25° C. in the same buffer containing 1 microCi/mil $^{45}$Ca. The membrane was then rinsed twice in 45% ethanol, blotted dry, and exposed to PhosphorImager screen, and the signal was read in Phosphorimager (Fuji Bas-1800).

CD Measurements-CD spectra were recorded on a Jasco J-715 spectropolarimeter at 25° C. with 7 accumulations. Cells of appropriate path lengths were used depending on the spectral region (0.02 and 2 cm for far- and near-UV CD, respectively). Far-UV CD spectra were recorded in the region of 195-250 nm. The ellipticity values were expressed in millidegrees.

Stains-all Binding Assay-Aliquots of protein solutions were added to the Stains-all solution and mixed gently. Circular dichroism induced in the achiral dye upon binding to the protein was measured in the visible region of the spectrum (400-700 nm). The dye solution and the crystallins were prepared in 2 mM MOPS buffer, pH 7.2, containing 30% ethylene glycol (34, 35). Ellipticities were expressed in millidegrees.

Fluorescence Spectroscopy-Fluorescence emission spectra were measured on a Hitachi F-4010 spectrofluorimeter. The intrinsic fluorescence of the proteins was recorded by exciting the solution at 295 nm and measuring the emission in the 310-400-nm region. All spectra were recorded in the correct spectrum mode with excitation and emission band passes of 5 nm each. Terbium binding experiments were done in 50 mM Tris, pH 6.4. Aliquots of terbium chloride (10 mM stock prepared in water) were added to the protein solution, and spectra were recorded.

Sequence Alignment and Molecular Modeling—The amino acid sequence of individual beta-gamma motifs of bovine beta-gamma-crystallin were aligned along with the members of the superfamily. The residues involved in calcium ligation were identified based on sequence homology with protein S and investigated in the crystal structure (Protein Data Bank code 4GCR.pdb) on a Silicon Graphics work station using software Molecular Simulations, Inc., San Diego. The position of calcium atom was fixed in space along with oxygen of side chain of amino acid residues that coordinate with it. Optimization and molecular dynamics operations were performed on this assembly.

BRIEF DESCRIPTION OF THE
ACCOMPANYING DRAWINGS

FIG. 1. shows $^{45}$Ca binding to gamma-crystallin. A, radioactive calcium ($^{45}$Ca) binding to gamma-crystallin was measured by the Hummel-Dreyer method (see Ref. 30). The column used was Sephadex G-25, equilibrated with 50 mM Tris buffer containing 50 mM NaCl, pH 7.1. Flow rate was adjusted to 5 ml/h. 60-μl aliquots were taken for radioactive counting. B, Klotz plot analysis of data collected from the Hummel-Dreyer chromatography runs, carried out at different free calcium concentrations (25-100 μM calcium chloride) containing $^{45}$Ca. A represents free calcium concentration; r, is the ratio of bound calcium to the total protein.

FIG. 2. shows Stains-all binding to gamma-crystallin. CD spectra of Stains-all induced upon binding to crystallin were recorded in 2 mM MOPS buffer, pH 7.2, containing 30% ethylene glycol, path length 1 cm. Dye concentration in all experiments was 16 μM. The ellipticity data are represented in millidegrees. A, CD spectra recorded with increasing concentration of -crystallin; 1, 0.026 mg/ml (---); 2, 0.078 mg/ml (- - -); 3, 0.13 mg/ml -.-.-. and 4, 0.156 mg/ml (. . .). B, effect of calcium on Stains-all--crystallin complex spectra. Calcium was added in the dye-protein mixture (-crystallin concentration was 115μ/ml), and CD was recorded. Calcium concentrations used are as follows: 1, no calcium (---); 2, 50 μM calcium (- - - -); 3, 100 μM calcium (. . .); 4, 200 μM calcium (-.-.-.); and 5, 300 μM calcium (-..-...). The J band was abolished with 300-μM calcium.

Figure 3:
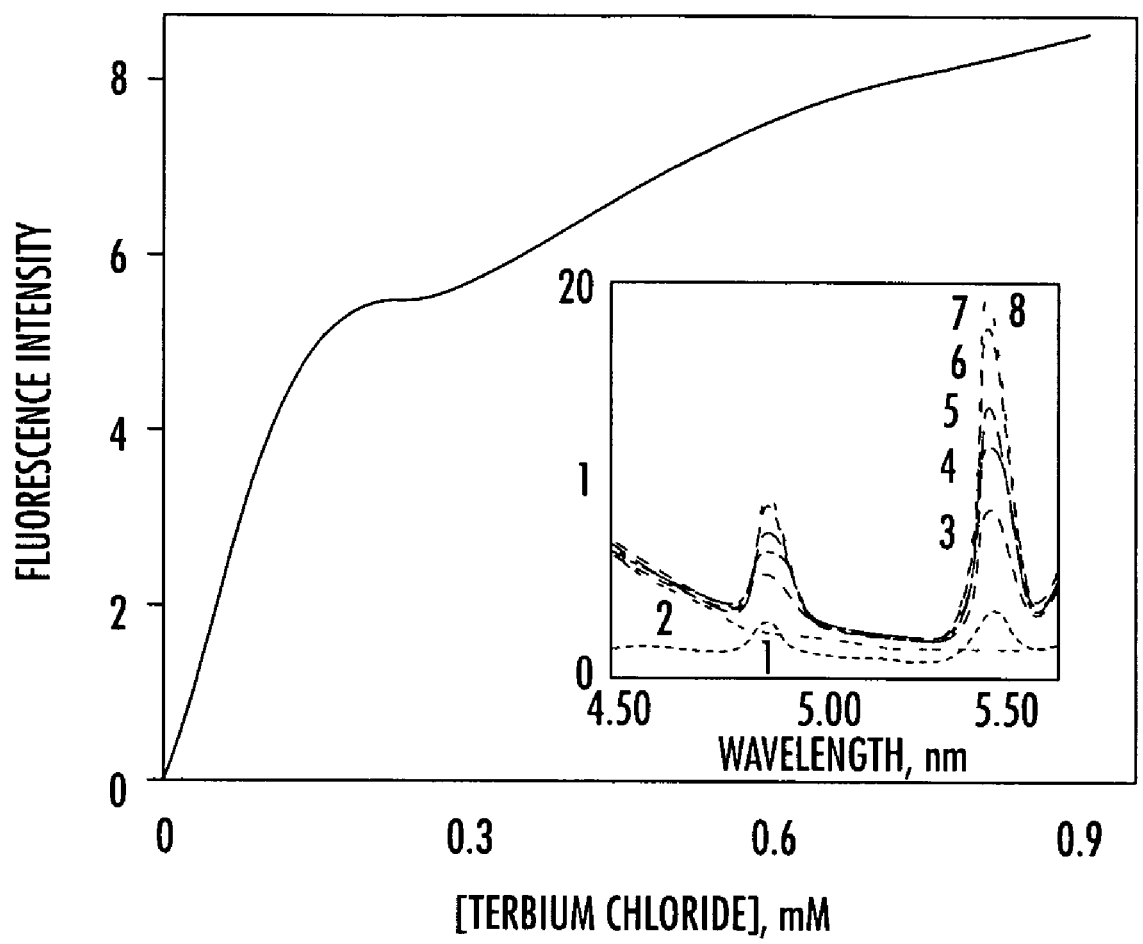

FIG. 3. shows Terbium ion binding to-gamma-crystallin. A solution of gamma-crystallin (440 μg/ml) was titrated with terbium chloride, and fluorescence emission spectra were recorded at excitation 285 nm. The fluorescence emission intensity at 545 nm was measured and plotted against terbium chloride concentration. Inset shows the increase in terbium fluorescence upon binding to gamma-crystallin, spectra 1 and 2 for terbium and protein only. Spectra 3-8 are with increasing concentrations of terbium chloride.

FIG. 4. shows putative calcium-binding sites in gamma-crystallin superfamily. Multiple sequence alignment of the crystallin domain of members of the superfamily is shown. Residues proposed to be involved in calcium binding are indicated by solid arrows showing the calcium-binding sites in members of the -crystallin superfamily. The conserved residues are shown in the boxes. Since the sequences of the domains are the repeats, the sequence of only one domain is aligned. PS, protein S; g, gamma-crystallin; BB2, beta-B2-crystallin.

Figure 5A:
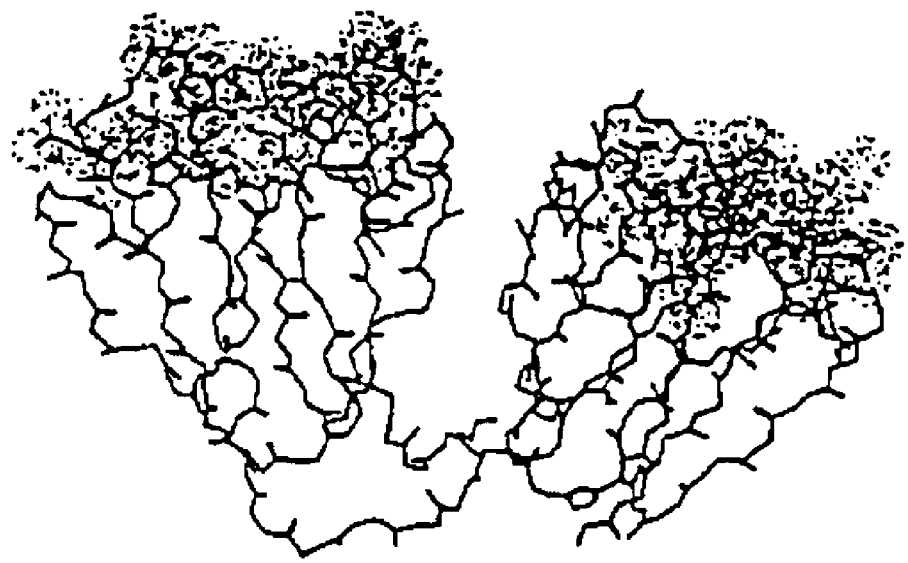
Figure 5B:
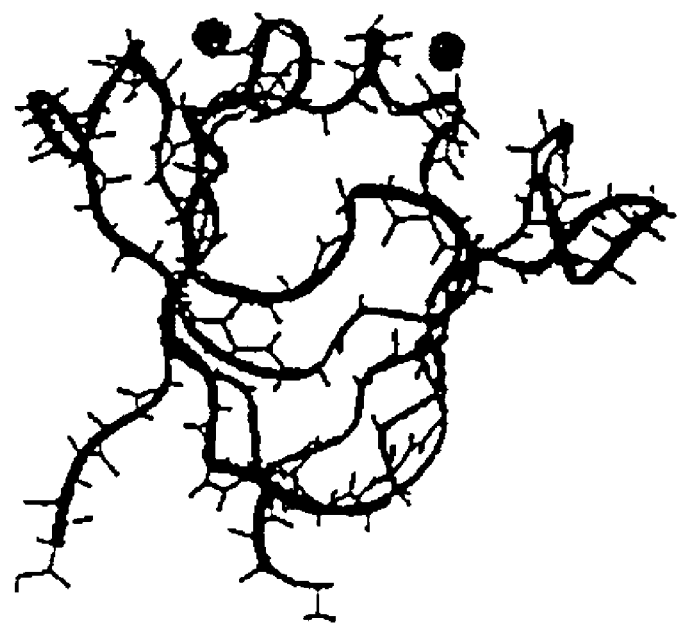

FIG. 5. shows molecular modeling of gamma-crystallin. a, the crystal structure of gamma-crystallin (Protein Data Bank code 4GCR.PDB) was retrieved from protein data bank. The residues involved in calcium binding are highlighted as electron density surface representations, and only the backbone of the rest of the molecule is shown. All four sites for calcium binding are shown. b, location of two calcium ions on the surface of two Greek key motifs of gamma-crystallin shown in the ribbon diagram. The energy minimization and dynamics was performed on the protein and calcium assembly.

Figure 6:
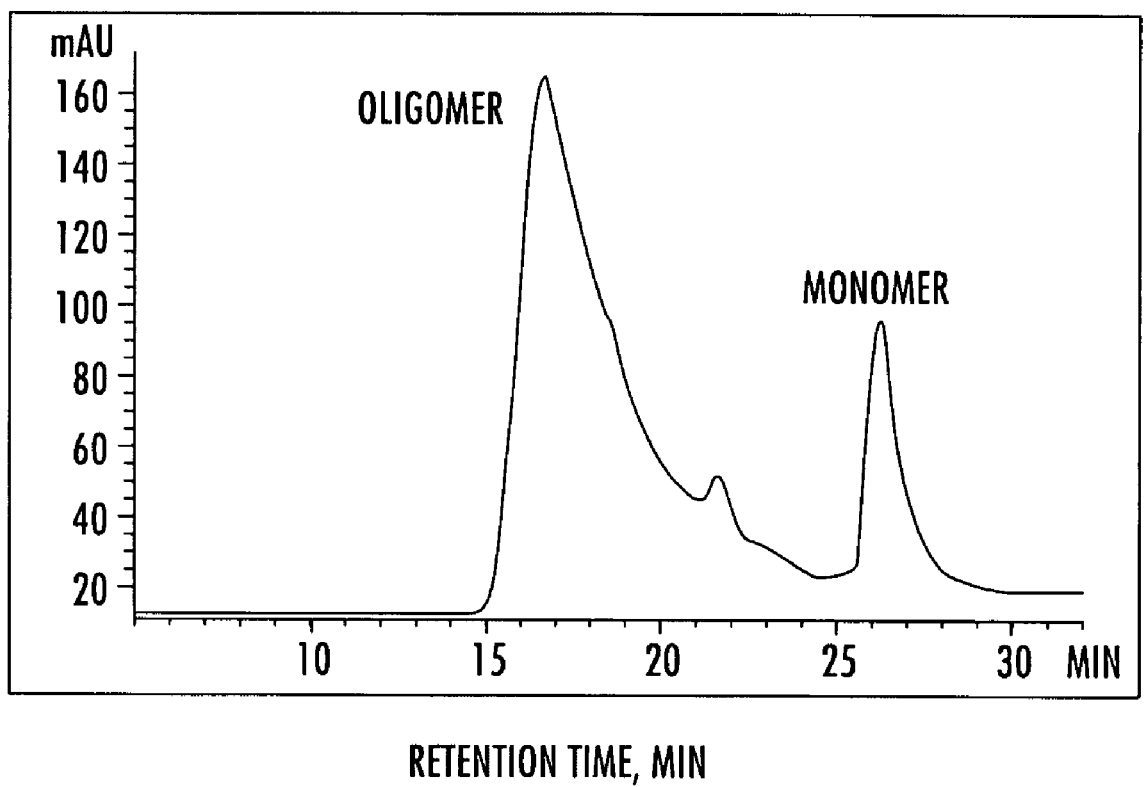

FIG. 6. shows Gel filtration HPLC of g3 peptide on Protein-Pak 125 column in 50 mM Tris buffer, pH 6.8, containing 50 mM NaCl.

FIG. 7. shows Far-UV CD of Greek key beta-sheet peptides. The peptides (5 μM) were dissolved in water, and CD was recorded in various methanol concentrations in 0.5-cm path length cell with 8 accumulations. a, g3 peptide: ---, 0; - - -, 40; -.-.-, 60; -..-..-, 80; and . . . ., 90% methanol; b, g3a peptide: ---, 0; - - -, 30; . . . ., 50; -.-.-, 70; and -..-...-; 90% methanol; c, g3b peptide: ---, 0; - - -, 30; -.-.-, 50; -..-..- , 70; and . . . ., 85% methanol; and d, s3a peptide: . . . ., 0; ---, 90% methanol.

Figure 8:
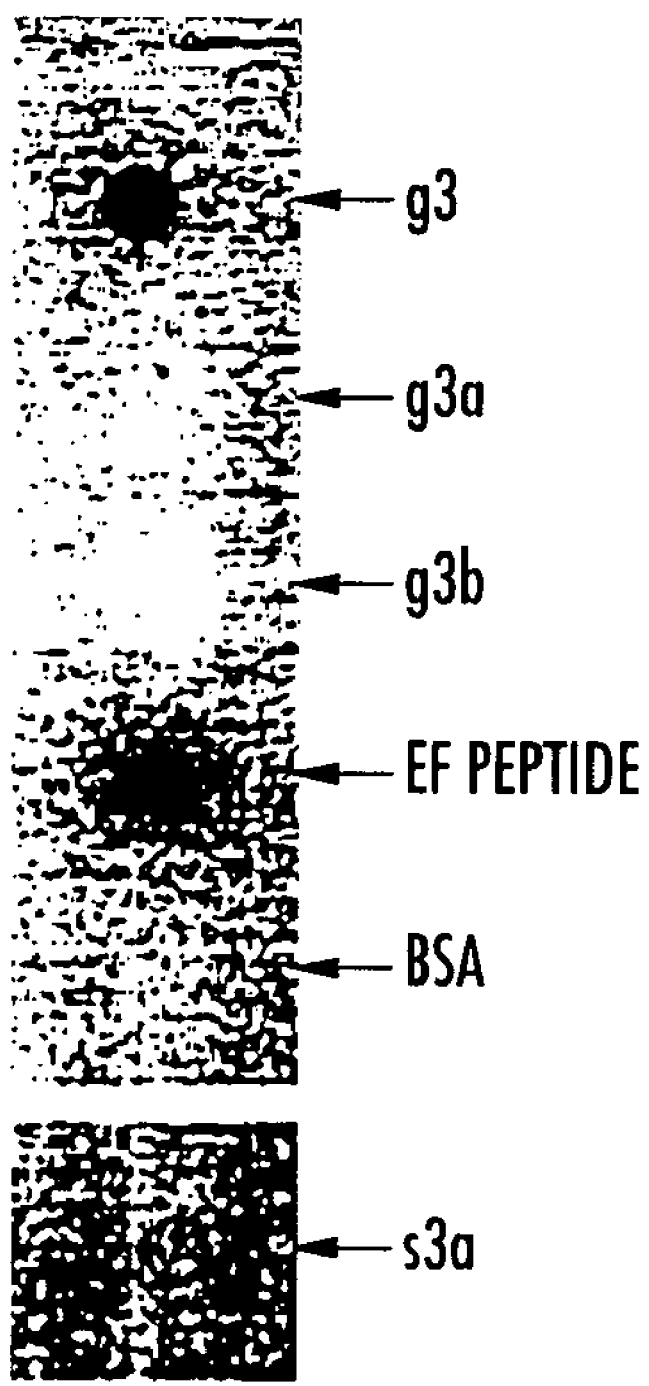

FIG. 8. shows Calcium binding to Greek key peptides by calcium overlay method. The wild type peptide g3, its variants (g3a and g3b) and s3a were spotted onto a polyvinylidene difluoride membrane and detected by $^{45}$Ca overlay. For a positive control, EF-hand peptide corresponding to site 4 of rat neuronal calcium sensor-1 was used; bovine serum albumin (BSA) was used as a negative control.

FIG. 9. shows Stains-all binding to Greek key peptides. CD spectra of Stains-all induced upon binding to peptides were recorded. Dye concentration in all experiments was 43 μM. The ellipticity data are represented in millidegrees. a, CD spectra were recorded with increasing concentration of the wild type peptide g3; 0.013 mg/ml (---), 0.037 mg/ml (- - -), and 0.057 mg/ml (. . . .). b, effect of calcium on Stains-all-peptide complex. Calcium was added to the dye-peptide mixture (peptide concentration was 57 μg/ml) and calcium concentrations used were: no calcium (---), 0.7 mM calcium (- - - -), and 7.5 mM calcium (. . . .). c and d represent the Stains-all binding of the modified peptides, g3a and g3b. Identical concentrations of dye and peptides were used.

RESULTS

Figure 1B:
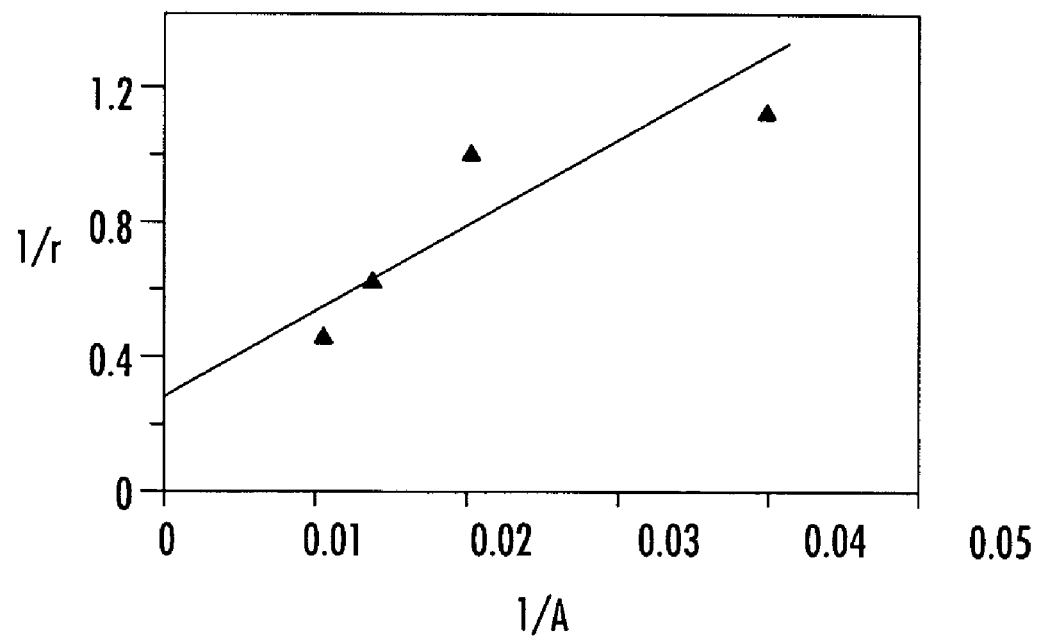

Probing Calcium Binding to gamma-Crystallin by Direct $^{45}$Ca Binding—The calcium binding to gamma-crystallin was performed by gel filtration method of Hummel-Dreyer (see Ref. 30). A representative Hummel-Dreyer gel elution chromatogram is shown in FIG. 1A. In a calcium-equilibrated column, a high radioactivity count at the protein elution peak (void volume), which quantitated calcium bound to the protein, was followed by a trough of low radioactivity count, which represented calcium depletion following calcium binding to the protein (FIG. 1A). The gel chromatography runs were repeated at $^{45}$Ca concentrations of 25, 50, 75, and 100 microM, keeping protein concentration constant. The dissociation constant, $K_D$, for gamma-crystallin was calculated by an inverse plot (31) from several chromatographic runs and found to be 90 microM, with 4 sites for metal binding (FIG. 1B). The calcium-binding affinity of gamma-crystallin (90 microM) was comparable to that of other members of this super-family (Table II).

TABLE II

| Proteins | Kp μM | Number of binding sites | Refs. |
|---|---|---|---|
| y-Crystallin | 90 | 4 | This work |
| βL-Crystallin | 170 | 4 | 18 |
| Protein S | 27, 76 | 4 | 6 |
| Spherulin 3a | 9,200 | 2 | 9 |

Figure 2A:
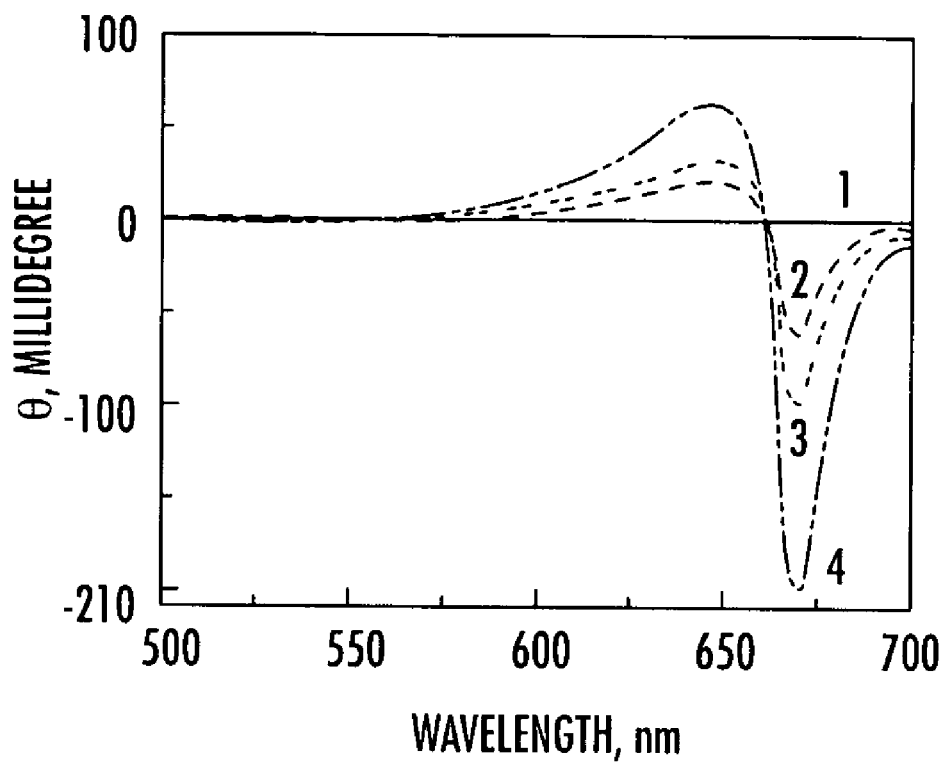

Probing Calcium Binding to gamma-Crystallin by Stains-all Interaction-We have used the calcium-mimic dye Stains-all as a reporter to study the calcium binding properties of gamma-crystallin. Stains-all displays distinct absorption and induced CD bands in the 480-660 nm region when it binds to $Ca^{2+}$-binding sites in proteins (34-37). We have reported earlier that Stains-all binds to beta and delta-crystallin, which induce the J and gamma bands of the dye, respectively (33, 35). FIG. 2A shows that Stains-all binds to y-crystallin and induces an intense J band at 670 nm. The intensity of this band increases if the dye/protein ratio is decreased. The binding is strong enough to be able to induce optical activity in the otherwise achiral dye. Upon addition of 50 microM calcium, the J band intensity is increased due to the conformational rearrangement, also shown by the individual EF-hand motifs of calcium-binding proteins (38). Upon further addition of calcium, the J band intensity decreases and is finally abolished in the presence of excess calcium (300 μM) (FIG. 2B).

Figure 2B:
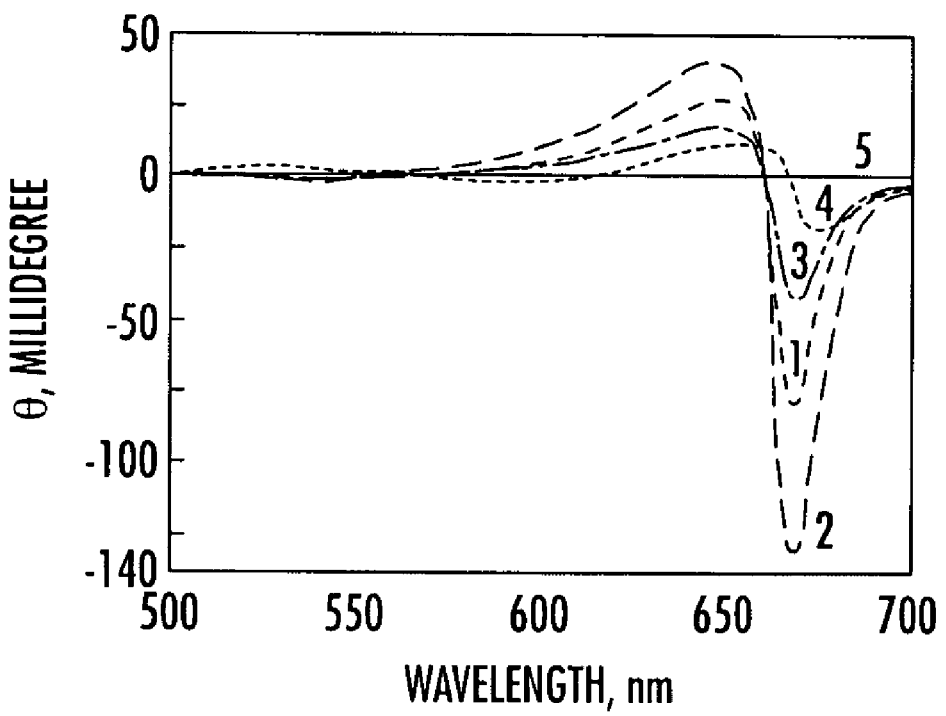

The abolition of the J band in the presence of calcium shows that the dye binds at the calcium binding sites in gamma-crystallin (FIG. 2B).

Probing Calcium Binding to gamma-Crystallin by Terbium Fluorescence-Calcium binding to gamma crystallin was probed using the luminescent lanthanide probe, $TbCl_3$. $Tb^{3+}$ is known to bind to Ca2+-binding sites and, as a consequence, displays enhanced luminescence in the visible region (39). The ionic size and binding characteristics of $Tb^{3+}$ are similar to those of the $Ca^{2+}$ ions (39). FIG. 3 shows that -crystallin enhances $Tb^{3+}$ fluorescence, suggesting that the protein binds the $Ca^{2+}$-mimic lanthanide ion. The dissociation constant for terbium binding to -crystallin was found to be about 300 µM. The presence of aromatic residues in the vicinity of the calcium-binding site is of interest, and one would expect an interaction between the aromatic rings and the bound metal ions. Indeed, when the $Ca^{2+}$-mimic $Tb^{3+}$ is used, we see the luminescence of the lanthanide activated upon exciting at 285 nm (aromatic absorption region), indicative of energy transfer at an estimated distance of 5 (40).

Identification of Greek Key Motif as Calcium-binding Sites in gamma-Crystallin—The above results clearly demonstrate that gamma-crystallin is a calcium-binding protein with four sites for ion binding. Since it has no EF-hand or any such known motif for calcium binding, we thought that four calcium-binding sites may be located in the four Greek keys. Based on sequence homology with protein S, we have identified Greek keys as calcium-binding sites in gamma-crystallin, as shown in FIG. 4. gamma-Crystallin shows 47% sequence homology as well as similarity in the structure of 4-fold repeats (13). The residues involved in calcium ligation in protein S are known from its crystal structure (27). The motifs 1 and 3 of gamma-crystallin are similar to motifs 2 and 4 in protein S, whereas motifs 2 and 4 of gamma-crystallin are similar to motifs 1 and 3 of protein S (13). The alignment of individual motifs of these proteins was used to identify the residues involved in calcium ligation, which shows that calcium-binding sites of gamma-crystallin are located within Greek key motifs. Based on sequence alignment, we find that the first calcium ligates at Glu-7, Arg-31, Asn-33, and Ser-30, whereas the second calcium binds at Glu-46, Arg-76, Ser-74, and Asp-73 (FIG. 4). All these residues are located at the surface of the structure, and their side chains are available for calcium binding (FIG. 5). Similarly, two other calcium-binding sites located at the C-terminal domain were also identified. The residues Glu-95, Thr-120, Glu-121, and His-123 form site 3, whereas Glu-136, Asn-162, Ala-163, and Gly-165 constitute site 4. The propensity of these residues for calcium ligation was investigated by molecular modeling. These residues were found to possess bond length and bond angles suitable for forming a bond for calcium binding to the oxygen atoms of the side chains of these residues (FIG. 5).

The Greek Key beta-Sheet Peptides, Structure and Conformation—In order to verify if the Greek key crystallin fold is a motif for calcium ion binding, we have synthesized four-stranded 42-residue -sheet peptide (peptide g3) corresponding to the third Greek key motif of -crystallin, and the first Greek key motif of spherulin 3a (residues 14-56) as control (Table I). To ascertain if the residues identified by alignment (above, and FIG. 4) participate in ligation, we have also synthesized several mutants of Greek key peptides (Table I). The two putative residues (Glu-95 and Glu-121), that were identified for calcium binding by homology with protein S, were modified to Lys in the peptide g3a (Table I). We have also investigated whether other acidic residues are involved in calcium binding (such as two aspartates at positions 108 and 109 are replaced by Lys in the peptide g3b).

Figure 7A:
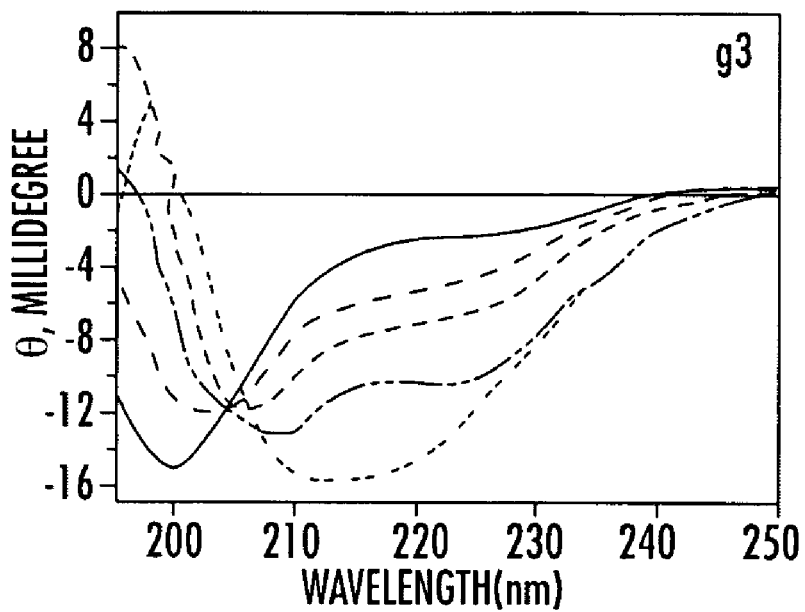
Figure 7B:
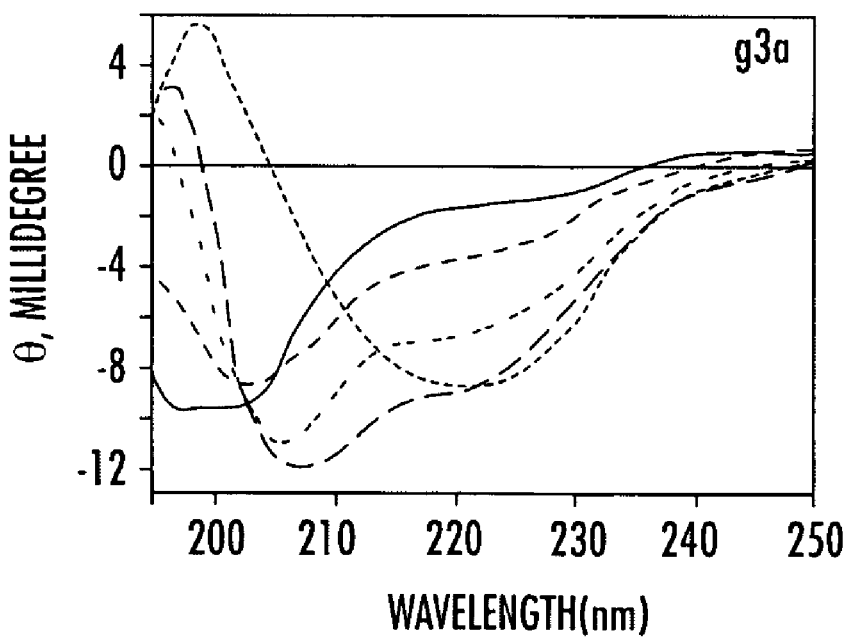
Figure 7C:
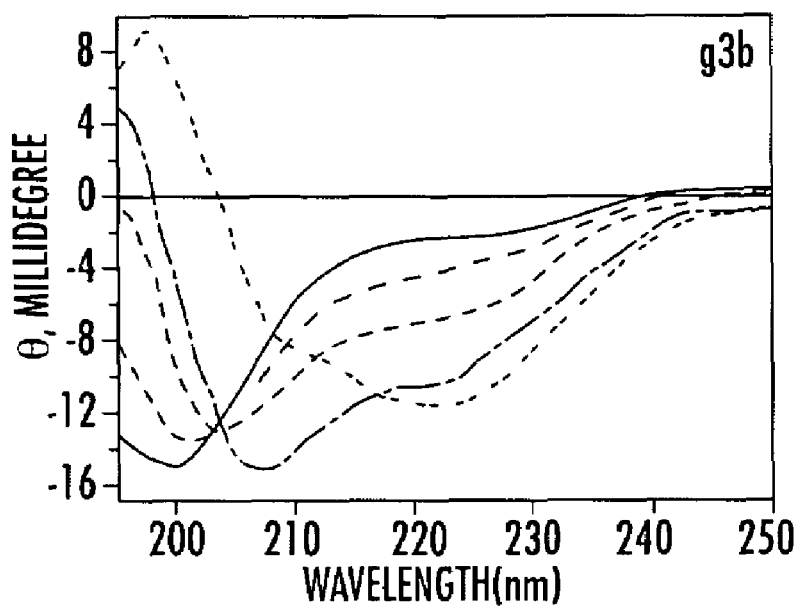
Figure 7D:
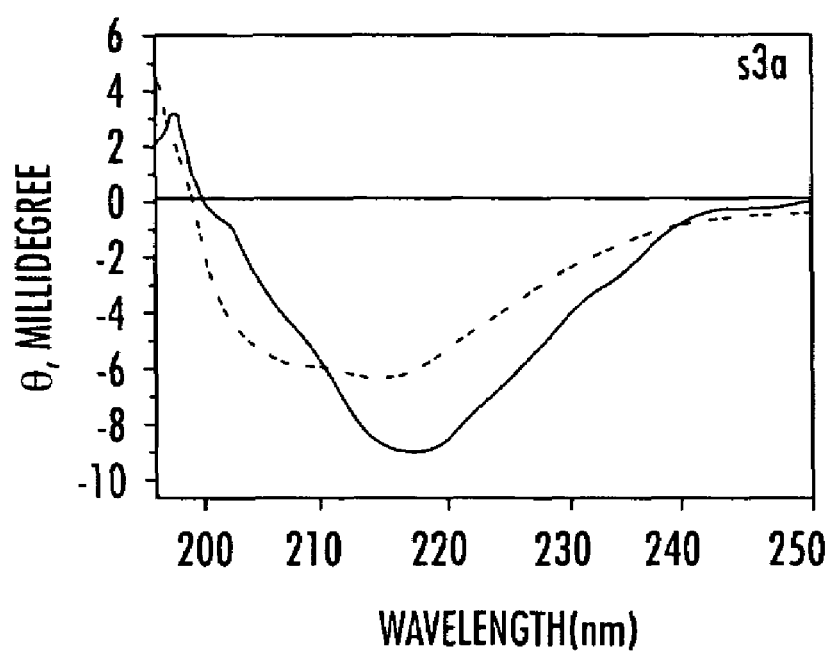

We have characterized and evaluated the secondary structure and aggregational propensity of these peptides by CD and HPLC. The wild type peptide g3 and its mutants are fairly soluble in aqueous medium. However, the peptide s3a is not soluble in water; it was solubilized in trifluoroethanol. These peptides form aggregates of various sizes as seen in their gel filtration profiles on HPLC (the chromatogram for g3 is shown as FIG. 6). All these peptides show a poorly organized, unfolded structure in aqueous solution. However, in increasing concentration of methanol, these peptides adopt beta-sheet conformation as shown by increasing ellipticity at 216 nm (FIG. 7, a-d). These peptides form well-defined-sheet conformation at >80% methanol/water mixture. The s3a peptide also exhibits beta-sheet conformation (FIG. 7d). The designed-sheet peptides have been shown earlier to possess unfolded structure in aqueous medium, which readily form -sheet in organic medium (41).

Probing Calcium Binding to Synthetic Greek Key Peptides by Direct $^{45}Ca$ Binding—The calcium binding to these Greek key peptides was performed by direct calcium binding using $^{45}Ca$ overlay method. FIG. 8 shows the peptide dot-blot for three peptides, g3, g3a, and g3b. To validate the procedure, we have used the peptide, corresponding to the EF4 of neuronal calcium sensor-1 (36 residues, residues 144-179) and the control peptide s3a. FIG. 8 shows that wild type peptide g3 binds calcium as strongly as the EF-hand peptide of neuronal calcium sensor-1. However, the two modified peptides (g3a and g3b) do not show detectable binding of $^{45}Ca$. These results show that an individual peptide corresponding to a Greek key is able to bind calcium and forms a complete unit in the same way as the EF-hand does, although the binding site geometry is different. The g3a peptide in which Glu-95 and Glu-121 residues were modified to Lys does not show any binding, indicating their participation in the binding. These residues were also investigated on the molecular model and were found to be able to show the geometry suitable for binding. The other peptide, g3b, also does not show any significant signal since the affinity was decreased due to the modification of aspartic acid residues 108 and 109 to Lys (FIG. 8).

Figures 9A, 9B, 9C, 9D:
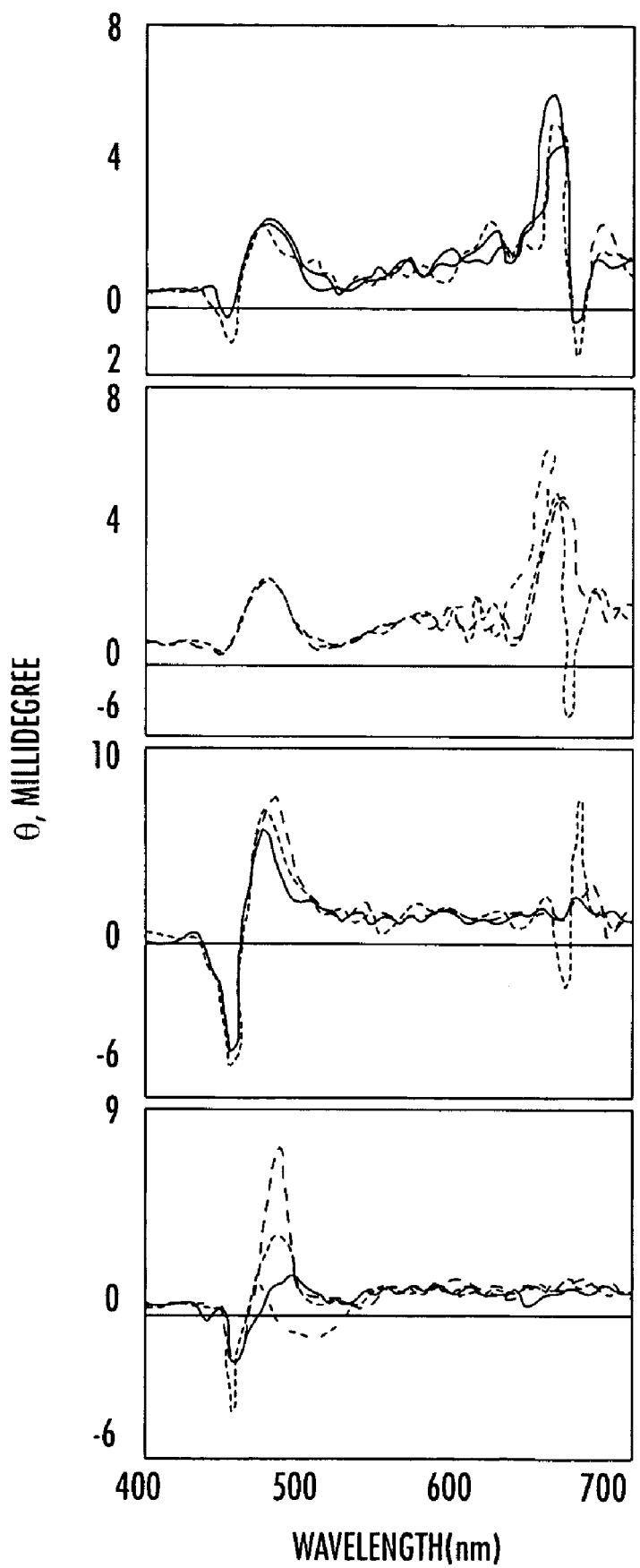

Probing Calcium Binding to Synthetic Greek Key Peptides by Calcium Probe Stains-all—The calcium binding to individual Greek key peptides was further evaluated using the more sensitive assay of Stains-all binding. This assay is suitable and convenient for comparing closely related calcium-binding proteins and peptides. A similar approach was used previously to study and compare the calcium binding properties of individual EF-hand peptides of calmodulin (38). The magnitude of the induced J or band is a direct indicator of the affinity toward calcium. The g3 peptide binds Stains-all and induces a strong J band and a weak band (FIG. 9a). The addition of calcium decreases the J band intensity. There is no induction of CD band in the peptide g3a and Stains-all complex at the higher dye:peptide ratio. However, the CD band induction is seen when higher concentrations of peptide are used (FIG. 9c). The binding of Stains-all to modified peptide g3a is decreased several fold indicating the role of these two amino acid residues in calcium binding (FIG. 9c). When dye binding was performed with peptide g3b, we found that this peptide binds the dye and induces the band indicating that it has not lost the calcium-binding ability completely, although the geometry and microenvironment of the binding site is altered due to modifications of acidic residues to basic residues (FIG. 9d). The addition of calcium in g3a and g3b peptides decreases the CD band intensity indicating the replacement of the dye. The control peptide, S3a, also binds the dye and induces a calcium-sensitive band at 470-475 nm.

These results show that although the $^{45}$Ca binding was not seen in the dot-blot assay for peptides g3a and g3b, we were able to see the dye binding indicating the decreased affinity. The affinity of these peptides calculated based on induced CD bands are in the order of g3>g3b>g3a.

Calcium Binding Does Not Influence Conformational Changes in Secondary Structure—Structural changes upon calcium binding to -crystallin were monitored by CD and fluorescence. gamma-Crystallin shows beta-sheet structure in the far-UV CD with a minimum at 218 nm. Addition of calcium does not induce any significant changes in the secondary and tertiary structures. Similar observations were also obtained for individual Greek key peptides. These results were confirmed by the inability of calcium to induce any change in protein Trp fluorescence. These results are relevant for a compact and stable protein such as -crystallin, which does not undergo conformational changes in tertiary structure upon calcium binding. It is relevant to mention that other proteins of the superfamily, protein S and beta-crystallin, also do not undergo any conformational changes upon binding calcium.

Discussion

We have probed calcium binding to gamma-crystallin both by direct (Hummel-Dreyer method using $^{45}$Ca) and indirect (terbium fluorescence and Stains-all interaction) methods. Gamma-Crystallin binds Tb$^{3+}$ and induces fluorescence through energy transfer from the two Trp present, one in each domain. It binds the calcium probe Stains-all in a calcium-dependent manner. We have also shown that a peptide corresponding to a Greek key crystallin fold is able to bind calcium, indicating this to be a site for ion binding. By mutating the potential residues, we have identified the amino acids, which participate in ligation. These results clearly show that gamma-crystallin is a calcium-binding protein, with binding affinity in the range of 90 μM and with 4 sites for calcium binding. The binding affinity of calcium to gamma-crystallin (90 μM) is more than that of -gamma crystallin (170 μM), another calcium-binding protein of the eye lens (6).

Crystallin Fold, a Motif for Calcium Ion Binding—For the first time, we have shown that the four-stranded Greek key beta-sheet peptide corresponding to crystallin fold forms an individual calcium-binding site. These peptides adopt beta-sheet conformation in water/methanol mixture and form aggregates producing anti-parallel beat-sandwich motif as shown by far-UV CD (FIG. 7). Our results of alignment of relevant regions of proteins that contain this fold and of four beta-stranded Greek key peptides used in this study (FIG. 4) show that the first calcium ligates at the residue next to the conserved aromatic amino acid of the sequence Y/F/WXXXXXXG, which is located at the end of the first-strand ("a" strand). The amino acid at this position is generally Asp, Asn, Glu, Gln, Ser, Tyr, and rarely Lys. Other three residues needed for calcium ligation lie just before the beginning of the fourth beta-strand (before the conserved Ser) and are usually Asp, Asn, Ser, Thr, Val, or Ala (FIG. 5). Clout et al. (42) have shown similarity in the calcium-binding sites in spherulin 3a and protein S and pointed out the role of these residues in ligation. Our results with Greek key peptides directly demonstrate the importance of these residues in ion binding. The role of conserved Ser in calcium ligation has already been shown earlier (14). Although there is a stretch of acidic residues in the "b" and "c" strands, they do not directly participate in the ion binding as shown in our results with peptide g3b. However, modifying the aspartate pair (Asp-108 and Asp-109) partially decreases the affinity toward calcium and alters the microenvironment of the peptide g3b as shown by Stains-all binding, since these residues are known to form a part of the cluster of alternate sign affecting the molecular surface (12).

gamma-Crystallin Superfamily Represents a Novel Class of Calcium-binding Protein Family-Our results demonstrate that Greek key crystallin fold forms a motif for calcium ion binding in -gamma crystallin superfamily. The calcium binding properties of protein S, beta-crystallin, and spherulin 3a have already been reported (6, 14, 17). Our results suggest that other proteins of the superfamily, which have not been shown so far to bind calcium, would also bind the cation. In fact, we have confirmed this point by studying another non-lens member of the superfamily, AIMI (absent in melanoma). We have found that a single crystallin domain of AIMI (1022-1117 residues), comprising two Greek keys, binds calcium with a comparative affinity to gamma-crystallin, which further corroborate our results.

The presence of topologically homologous residues in members of the superfamily makes us suggest that this family represents a novel class of calcium-binding proteins. Conformationally, these are all-proteins, and the binding site is located within the Greek key topology. As the geometry of this motif is distinct from that of the other calcium-binding motifs, we propose that the crystallin fold is a novel calcium-binding motif. It is interesting to note that calcium binding does not induce marked changes in crystallin conformation, which may be due to the stable and compact structure of the fold. However, the stability of gamma-crystallin is increased in the presence of calcium ions, which suggests that the presence of calcium restricts unfolding (2). Two other proteins of the superfamily, protein S and spherulin 3a, also exhibit a similar enhancement in the stability upon calcium binding (43, 44). Members of this family may act as a buffer in the set processes dealing with the uptake, sequestration, and transport of calcium ions, since calcium-binding changes are larger in the sensor proteins than in buffer proteins. In the physiological context, the calcium binding properties of beta and gamma-crystallins would ensure that cytosolic levels of calcium in the lens are maintained in a steady or homeostatic condition, since any change in free calcium levels can lead to opacification (1, and 2). As the eye lens ages or turns cataractous, structural alterations and damage occur to its components, including the crystallins. These would be expected to lead to alterations in the Ca$^{2+}$-binding and storing ability of these molecules and to the release of Ca$^{2+}$ ions, which would in turn trigger lens opacification.

REFERENCES

1. Duncan, G., and Jacob, T. J. C. (1984) *CIBA Found. Symp.* 206, 132-152
2. Duncan, G., Williams, M. R., and Riach, R. A. (1994) *Prog. Retinal Eye Res.* 13, 623-650
3. Vrensen, G. F. J. M., Sanderson, J., Willekens, B., and Duncan, G. (1995) *Investig. Opthalmol. Vis. Sci.* 36, S198
4. Vrensen, G. F. J. M., and DeWolf, A. (1996) *Ophthalmic Res.* 28, 78-85
5. Van Marie, J., Jonges, R., Vrensen, G. F. J. M., and DeWolf, A. (1997) *Exp. Eye Res.* 65, 83-88
6. Sharma, Y., Rao, C. M., Narasu, M. L., Rao, S. C., Somasundaram, T., Gopalakrishna, A., and Balasubramanian, D. (1989) *J. Biol. Chem.* 264, 12794-12799
7. Balasubramanian, D., and Sharma, Y. (1991) in *Novel Calcium-binding Proteins: Fundamentals and Clinical Implications* (Heizmann, C. W., ed) pp. 361-374, Springer-Verlag, Berlin 8. Blundell, T., Lindley, P., Miller, L., Moss, D. Slingsby, C., Tickle, I. Turoell, B., and Wistow, G. (1981) *Nature* 289, 771-777
9. Wistow, G., Turnell, B., Summers, L., Slingsby, C., Moss, D., Miller, L., Lindley, P., and Blundell, T. (1983) *J. Mol. Biol.* 170, 175-202
10. Wistow, G., and Piatigorsky, J. (1988) *Ann. Rev. Biochem.* 67, 479-504
11. Hemmingsen, J. M., Geraert. K. M., Richardson, J. S., and Richardson, D. C. (1994) Protein Sci. 3, 1927-1937
12. Chirgadze, Y. N., and Tabolina, 0. Y. (1996) *Protein Eng.* 9, 745-754
13. Wistow, G., Summers, L., and Blundell, T. (1985) *Nature* 315, 771-773
14. Teintze, M., Inouye, S., and Inouye, M. (1988) *J. Biol. Chem.* 263, 1199-1203
15. Bagby, S., Harvey, T. S., Eagle, S. G., Inouye, S., and Ikura, M. (1994) *Proc. Natl. Acad. Sci. U.S.A.* 91, 4308-4312
16. Wistow, G. (1990) *J. Mol. Evol.* 30, 140-145
17. Rosinke, B., Renner, C., Mayr, E.-M., Jaenicke. R., and Holak, T. A. (1997) *J. Mol. Biol.* 271, 645-655
18. Ray, M. E., Wistow, G., Su, Y. A., Meltzer, P. S., and Trent, J. M. (1997) *Proc. Natl. Acad. Sci. U.S.A.* 94, 3229-3234
19. Wistow, G., Jaworaki, C., and Rao, P. V. (1995) *Exp. Eye Res.* 61, 637-639
20. Ogawa, M., Takabatake, T., Takahaahi, T. C., and Takeshima. K. (1997) *Dea. Genes Evol.* 206, 417-424
21. Ogawa, M., Takahashi, T. C., Takabatake, T., and Takeshima, K. (1998) *Dev. Growth & Differ.* 40, 465-473
22. Antuch, W., Guntert, P., and Wuthrich, K. (1996) *Nat. Struct. Biol.* 3, 662-665
23. Ohno, A., Tate. S.-I., Seeram, S. S., Hiraga, K., Swindells, M. B., Oda, K., and Kainosho, M. (1998) *J. Mol. Biol.* 282, 421-433
24. Chan, C. W., Saimi, Y., and Rung, C. (1999) *Gene (Amst.)* 231, 21-32
25. Lubsen, N. H., Aarts, H. J. M., and Shoenmakers, J. G. G. (1988) *Prog. Biophys. Mol. Biol.* 61, 47-76
26. Shanna, Y., and Balasubramanian, O. (1996) *Ophthalmic Res.* 28, 44-47
27. Wenk, M., Baumgarten, R., Holak, T. A., Huber, R., Mayr, E. M., and Jaenicke, R. (1999) *J. Mol. Biol.* 288, 1533-1545
28. Memfield, R. B. (1969) *Adv. Emymol.* 32, 221-296
29. Fairwell, T., Hospattankar, A. V., Brewer, H. B., and Khan, S. A. (1987) *Proc. Natl. Acad. Sci. U.S.A.* 84, 4796-4800
30. Hummel, J. P., and Dreyer, W. J. (1962) *Biochim. Biophys. Acta* 63, 530-532
31. Klotz, I. M. (1948) *J. Am. Chem. Soc.* 70, 939-944
32. Klotz, I. M., and Hunston, D. L. (1984) *J. Biol. Chem.* 259, 10060-10062
33. Maruyama, K., Mikawa, T., and Ebashi, S. (1984) *J. Biochem.* (Tokyo) 95, 511-619
34. Caday. C. G., and Steiner, R. F. (1985) *J. Biol. Chem.* 260, 5985-5990
35. Sharma, Y., Rao, C. M., Rao, C. S., Somasundaram, T., Gopalakrishna, A., and Balasubramanian, D. (1989) *J. Biol. Chem.* 264, 20923-20927
36. Caday, C. G., Lambooy, P. K., and Steiner, R. F. (1986) *Biopolymers* 25, 1579-1595
37. Sharma, Y., and Balaaubramanian, D. (1991) in *Novel Calcium-binding Proteins: Fundamentals and Clinical Implications* (Heizmann, C. W., ed) pp. 51-61, Springer-Verlag, Berlin
38. Sharma, Y., Chandani, S., Sukhaswami, M. B., Uma, L., Balasubramanian, D., and Fairwell, T. (1997) *Eur. J. Biochem.* 243, 42-48
39. Brittain, H. G., Richardson, F. S., and Martin, R. B. (1976) *Am. Chem. Sac.* 98,
40. Horrocks, W. D. (1993) *Methods Ewymol.* 226, 495-538
41. Das, C., Nayak, V., Raghothama, S., and Balaram, P. (2000) *J. Pept. Res.* 56, 307-317
42. Clout, N. J., Kretschmar, M., Jaenicke, R., and Slingsby, C. (2001) *Structure* 9, 115-124
43. Wenk, M., and Mayr, E.-M. (1998) *Eur. J. Biol.* 255, 604-610
44. Kretschmar, M., Mayr, E.-M., and Jaenicke, R. (1999) *J. Mol. Biol.* 289, 701-705

The invention claimed is:

1. A method of identifying calcium binding sites in gamma-crystallin useful in calcium-based homeostasis for the management of Cataract, the method being performed on a suitably programmed computer, said method comprising steps of:
   a) isolating gamma-crystallin from eye lens,
   b) analyzing binding of calcium to the isolated gamma-crystallin protein, identifying a Greek key Motif as a calcium-binding site in the gamma crystalline, and
   c) producing an output of the calcium-binding site, wherein the output is displayed to a user.

2. A method as claimed in claim 1, wherein the binding of calcium does not affect conformation of secondary and tertiary structure of the protein.

3. A method as claimed in claim 1, wherein the calcium binding site is adjacent to a conserved aromatic corner of any one of the following amino acid sequences: YXXXXXXG, FXXXXXXG or WXXXXXXG, which are located at the end of the first beta-strand.

4. A method as claimed in claim 1, wherein gamma crystallin represents a novel class of calcium binding proteins.

5. A method as claimed in claim 1, wherein the protein shows four sites of calcium binding.

6. A method as claimed in claim 1, wherein the Greek key motif is the site for ion-exchange.

7. A method as claimed in claim 3, wherein the amino-acid X is selected from the group comprised of Asp, Asn, Glu, Gln, Ser, Tyr, and Lys.

8. A method as claimed in claim 7, wherein there are three other residues needed for calcium ligation and the three other residues lie just before the beginning of the fourth beta-strand and are Asp, Asn, Thr, Val, or Ala.

9. A method as claimed in claim 1, wherein the Greek-key motif is a novel calcium-binding motif.

10. A method as claimed in claim 1, wherein stability of gamma-crystallin increases in the presence of calcium ions.

11. A method as claimed in claim 1, wherein calcium binding ensures steady cytosolic level of calcium.

12. The method of claim 1, wherein the output is stored to a data repository.

* * * * *

SEQUENCE LISTING

```
<160> NUMBER OF SEQ ID NOS: 18

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Met Arg Ile Tyr Glu Arg Asp Asp Phe Arg Gly Gln Met Ser Glu
1               5                   10                  15

Ile Thr Asp Asp Cys Pro Ser Leu Gln Asp Arg Phe His Leu Thr Glu
            20                  25                  30

Val His Ser Leu Asn Val Leu Glu Gly Ser
        35                  40

<210> SEQ ID NO 2
<211> LENGTH: 42
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Arg Met Arg Ile Tyr Lys Arg Asp Asp Phe Arg Gly Gln Met Ser Glu
 1               5                  10                  15

Ile Thr Asp Asp Cys Pro Ser Leu Gln Asp Arg Phe His Leu Thr Lys
            20                  25                  30

Val His Ser Leu Asn Val Leu Glu Gly Ser
        35                  40

<210> SEQ ID NO 3
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Met Arg Ile Tyr Glu Arg Asp Asp Phe Arg Gly Gln Met Ser Glu
 1               5                  10                  15

Ile Thr Lys Lys Cys Pro Ser Leu Gln Asp Arg Phe His Leu Thr Glu
            20                  25                  30

Val His Ser Leu Asn Val Leu Glu Gly Ser
        35                  40

<210> SEQ ID NO 4
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Glu Val Phe Leu Tyr Lys His Val Asn Phe Gln Gly Asp Ser Trp
 1               5                  10                  15

Lys Val Thr Gly Asn Val Tyr Asp Phe Arg Ser Val Ser Gly Leu Asn
            20                  25                  30

Asp Val Val Ser Ser Val Lys Val Gly Pro Asn
        35                  40

<210> SEQ ID NO 5
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Asn Ile Thr Val Phe Tyr Asn Glu Asp Phe Gln Gly Lys Gln Val
 1               5                  10                  15

Asp Leu Pro Pro Gly Asn Tyr Thr Arg Ala Gln Leu Ala Ala Leu Gly
            20                  25                  30

Ile Glu Asn Asn Thr Ile Ser Ser Val Lys Val Pro Pro
        35                  40                  45
```

```
<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Cys Trp Met Leu Tyr Glu Arg Pro Asn Tyr Gln Gly His Gln Tyr
 1               5                  10                  15

Phe Leu Arg Arg Gly Asp Tyr Pro Asp Tyr Gln Gln Trp Met Gly Phe
            20                  25                  30

Asn Asp Ser Ile Arg Ser Cys Arg Leu Ile
        35                  40

<210> SEQ ID NO 7
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Arg Ala Arg Phe Phe Tyr Lys Glu Gln Phe Asp Gly Lys Glu Val
 1               5                  10                  15

Asp Leu Pro Pro Gly Gln Tyr Thr Gln Ala Glu Leu Glu Arg Tyr Gly
            20                  25                  30

Ile Asp Asn Asn Thr Ile Ser Ser Val Lys Pro Gln Gly
        35                  40                  45

<210> SEQ ID NO 8
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Trp Val Leu Tyr Glu Met Pro Ser Tyr Arg Gly Arg Gln Tyr
 1               5                  10                  15

Leu Leu Arg Pro Gly Glu Tyr Arg Arg Tyr Leu Asp Trp Gly Ala Met
            20                  25                  30

Asn Ala Lys Val Gly Ser Leu Arg Arg Val Met
        35                  40

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Lys Ala Ile Leu Tyr Gln Asn Asp Gly Phe Ala Gly Asp Gln Ile
 1               5                  10                  15

Glu Val Val Ala Met Ala Glu Glu Leu Gly Pro Leu Asn Asn Asn Val
            20                  25                  30

Ser Ser Ile Arg Val Ile Ser
        35
```

```
<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Lys Ile Thr Phe Tyr Glu Asp Arg Gly Phe Gln Gly His Cys Tyr
 1               5                  10                  15

Glu Cys Ser Ser Asp Cys Pro Asn Leu Gln Pro Tyr Phe Ser Arg Cys
            20                  25                  30

Asn Ser Ile Arg Val Asp Ser
        35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Ala Val Val Leu Phe Lys Asn Asp Asn Phe Ser Gly Asp Thr Leu
 1               5                  10                  15

Pro Val Asn Ser Asp Ala Pro Leu Thr Gly Ala Met Asn Asn Asn Thr
            20                  25                  30

Ser Ser Ile Arg Ile Ser
        35

<210> SEQ ID NO 12
<211> LENGTH: 41
<212> TYPE: PRT
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: MOD_RES
<222> LOCATION: (10)
<223> OTHER INFORMATION: Ornithine

<400> SEQUENCE: 12

Phe Arg Met Arg Ile Tyr Glu Arg Asp Xaa Phe Arg Gly Gln Met Ser
 1               5                  10                  15

Glu Ile Thr Asp Asp Cys Pro Ser Leu Gln Asp Arg Phe His Leu Thr
            20                  25                  30

Glu Val His Ser Leu Asn Val Leu Glu
        35                  40

<210> SEQ ID NO 13
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 13

Asn Thr Ile Thr Val Tyr Glu His Ser Asp Phe Arg Gly Leu Tyr Lys
  1               5                  10                  15

Thr Phe Thr Ser Asp Val Pro Asn Leu Val Tyr Glu Asn Phe Asn Asp
             20                  25                  30

Cys Ile Ser Ser Val Lys Ile Ala Gly
         35                  40

<210> SEQ ID NO 14
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Thr Ile Thr Val Tyr Glu His Pro Asn Phe Gln Gly Leu Ser Arg
  1               5                  10                  15

Thr Phe Thr Thr Asp Val Pro Arg Leu Ser Glu His Ser Phe Glu Asp
             20                  25                  30

Cys Ile Ser Ser Ala Lys Val Val Gly
         35                  40

<210> SEQ ID NO 15
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Thr Ile Thr Val Tyr Glu His Ser Asn Phe Gln Gly Leu His Lys
  1               5                  10                  15

Thr Phe Thr Ala Asp Val Pro Asn Leu Val Asn Glu Ser Phe Asn Asp
             20                  25                  30

Cys Ile Ser Ser Val Lys Ile Val Gly
         35                  40

<210> SEQ ID NO 16
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Lys Ile Ile Ile Phe Glu Gln Glu Asn Phe Gln Gly His Ser His
  1               5                  10                  15

Glu Leu Asn Gly Pro Cys Pro Asn Leu Lys Glu Thr Gly Val Glu Lys
             20                  25                  30

Ala Gly Ser Val Leu Val Gln Ala
         35                  40

<210> SEQ ID NO 17
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 17

Gly Cys Ala Thr Ile Trp Glu Gly Ser Gly Cys Val Gly Arg Ser Thr
1               5                   10                  15

Thr Met Cys Cys Pro Ala Asn Thr Cys Cys Asn Ile Asn Thr Gly Phe
                20                  25                  30

Tyr Ile Arg Ser Tyr Arg Arg Val Glu
            35                  40

<210> SEQ ID NO 18
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Val Trp Val Ala Tyr Glu Asn Pro Asp Phe Thr Gly Glu Gln Tyr
1               5                   10                  15

Ile Leu Asp Lys Gly Phe Tyr Thr Ser Phe Glu Asp Trp Gly Gly Lys
                20                  25                  30

Asn Tyr Lys Ile Ser Ser Val Gln Pro
            35                  40
```